US009999402B2

(12) United States Patent
Chevion et al.

(10) Patent No.: US 9,999,402 B2
(45) Date of Patent: Jun. 19, 2018

(54) AUTOMATIC IMAGE SEGMENTATION

(71) Applicant: International Business Machines Corporation, Armonk, NY (US)

(72) Inventors: Dan Chevion, Haifa (IL); Pavel Kisilev, Maalot (IL); Boaz Ophir, Haifa (IL); Eugene Walach, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 268 days.

(21) Appl. No.: 14/335,960

(22) Filed: Jul. 21, 2014

(65) Prior Publication Data
US 2016/0015360 A1   Jan. 21, 2016

(51) Int. Cl.
*A61B 8/08* (2006.01)
*G06T 7/11* (2017.01)
*G06T 7/12* (2017.01)
*G06T 7/187* (2017.01)

(52) U.S. Cl.
CPC ............... *A61B 8/085* (2013.01); *G06T 7/11* (2017.01); *G06T 7/12* (2017.01); *G06T 7/187* (2017.01); *A61B 8/0825* (2013.01); *A61B 8/5223* (2013.01); *G06T 2207/10132* (2013.01); *G06T 2207/20156* (2013.01); *G06T 2207/30096* (2013.01)

(58) Field of Classification Search
CPC ..... A61B 8/0825; A61B 8/085; A61B 8/5223; G06T 2207/10132; G06T 2207/20112; G06T 2207/30096; G06T 7/0012; G06T 7/004; G06T 7/0083
See application file for complete search history.

(56) References Cited

U.S. PATENT DOCUMENTS 5,984,870 A * 11/1999 Giger ................... G06T 7/0012
                                                    600/443
7,466,848 B2   12/2008 Metaxas et al.
8,265,355 B2    9/2012 Zhao et al.
(Continued)

FOREIGN PATENT DOCUMENTS

EP       1988507       9/2010
WO    2012/112627      8/2012
WO    2012/163613     12/2012

OTHER PUBLICATIONS

Shrinath et al., "Segmentation of ultrasound breast images using vector neighborhood with vector sequencing on KMCG and augmented KMCG algorithms", IJACSA International Journal of Advanced Computer Science and Applications, vol. 4, No. 2, 2013.
(Continued)

*Primary Examiner* — Katherine Fernandez
(74) *Attorney, Agent, or Firm* — Ziv Glazberg (57) ABSTRACT

A computer implemented method, a computerized system and a computer program product for automatic image segmentation. The computer implemented method comprises obtaining an image of a tissue, wherein the image is produced using an imaging modality. The method further comprises automatically identifying, by a processor, a tissue segment within the image, wherein said identifying comprises identifying an artifact within the image, wherein the artifact is a misrepresentation of a tissue structure, wherein the misrepresentation is associated with the imaging modality; and searching for the tissue segment in a location adjacent to the artifact.

12 Claims, 3 Drawing Sheets

(56) References Cited

U.S. PATENT DOCUMENTS

| | | | |
|---|---|---|---|
| 8,517,945 B2 | 8/2013 | Huo et al. | |
| 2003/0161513 A1* | 8/2003 | Drukker | G06T 7/0012 |
| | | | 382/128 |
| 2005/0027188 A1* | 2/2005 | Metaxas | A61B 5/055 |
| | | | 600/410 |
| 2010/0121178 A1 | 5/2010 | Krishnan et al. | |
| 2010/0158332 A1* | 6/2010 | Rico | A61B 5/4312 |
| | | | 382/128 |
| 2012/0128224 A1 | 5/2012 | Yu et al. | |
| 2012/0243757 A1* | 9/2012 | Funka-Lea | G06T 7/0002 |
| | | | 382/131 |
| 2013/0144167 A1* | 6/2013 | Lee | A61B 8/085 |
| | | | 600/443 |
| 2016/0317130 A1* | 11/2016 | Auvray | G06T 7/0012 |

OTHER PUBLICATIONS

Gupta et al., "Automatic breast lesion segmentation and scoring in color elastography images", Philips Electronics India Limited, Bangalore, 2013. Can be found at : http://home.iitk.ac.in/~gnitish/docs/philips.pdf.

Guo et al, "A novel approach to breast ultrasound image segmentation based on the characteristics of breast tissue and particle Swarm Optimization", Proceedings of the 11th Joint Conference on Information Sciences, pp. 1-5, 2008.

Massich et al., "Lesion segmentation in breast sonography", Digital Mammography, Lecture Notes in Computer Science vol. 6136, 2010, pp. 39-45.

\* cited by examiner

AUTOMATIC IMAGE SEGMENTATION

TECHNICAL FIELD

The present disclosure relates to automatic image segmentation in general, and to automatic image segmentation based on artifact identification, in particular.

BACKGROUND

Medical imaging is the technique, process and art of creating visual representations of the interior of a body for clinical analysis and medical intervention. Medical imaging seeks to reveal internal structures hidden by the skin and bones, as well as to diagnose and treat disease. Medical imaging may also be used to establish a database of normal anatomy and physiology to make it possible to identify abnormalities.

One example of medical imaging may be ultrasonography which is a technique that is based on ultrasound waves and which helps physicians to visualize the structures of internal organs of human body.

In some cases it is difficult to identify the boundaries of abnormal regions in the image. Hence segmentation may be desired. The manual methods of segmentation may require high attention of sonographer, may suffer from poor accuracy, be prone to human error and may be time consuming. Automatic segmentation of medical imaging products can help the physicians by locating abnormal regions in the image.

BRIEF SUMMARY

One exemplary embodiment of the disclosed subject matter is a computer implemented method comprising obtaining an image of a tissue, wherein the image is produced using an imaging modality. The method further comprising automatically identifying, by a processor, a tissue segment within the image, wherein said identifying comprises identifying an artifact within the image, wherein the artifact is a misrepresentation of a tissue structure, wherein the misrepresentation is associated with the imaging modality; and searching for the tissue segment in a location adjacent to the artifact.

Another exemplary embodiment of the disclosed subject matter is a computerized apparatus having a processor, the processor being adapted to perform the steps of: obtaining an image of a tissue, wherein the image is produced using an imaging modality; automatically identifying, by a processor, a tissue segment within the image, wherein said identifying comprises identifying an artifact within the image, wherein the artifact is a misrepresentation of a tissue structure, wherein the misrepresentation is associated with the imaging modality; and searching for the tissue segment in a location adjacent to the artifact.

Yet another exemplary embodiment of the disclosed subject matter is a computer program product comprising a computer readable storage medium retaining program instructions, which program instructions when read by a processor, cause the processor to perform a method comprising: obtaining an image of a tissue, wherein the image is produced using an imaging modality; automatically identifying, by a processor, a tissue segment within the image, wherein said identifying comprises identifying an artifact within the image, wherein the artifact is a misrepresentation of a tissue structure, wherein the misrepresentation is associated with the imaging modality; and searching for the tissue segment in a location adjacent to the artifact.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

One technical problem dealt with by the disclosed subject matter is to automatically identify a tissue segment within an image produced using an imaging modality. In some exemplary embodiments, identifying the tissue segment within the image may comprise finding the tissue segment's exact location within the image. Additionally or alternatively, identifying the tissue segment within the image may comprise identifying the tissue segment's exact margins.

In some exemplary embodiments, the image may be a medical image. In some exemplary embodiment, the tissue segment which is being located may be a tumor within the tissue.

There may be several imaging modalities for creating medical imaging, such as: Radiography, Magnetic Resonance Imaging (MRI), Nuclear Imaging, Ultrasound, Elastography, Tactile Imaging, Photoacoustic imaging, Thermography, Tomography, Echocardiography, Functional near-infrared Spectroscopy, or the like.

In some exemplary embodiments, the image may be an ultrasonic image, which may be created using ultrasound waves emitted from a source, and recording the echo returning from within a body. The ultrasound waves may reflect and may echo off parts of the tissue; the echo may be recorded and may be used to generate the ultrasonic image.

The ultrasonic image may be produced using a brightness-mode ultrasound imaging modality, also known as B-mode. Brightness mode may provide structural information utilizing different shades of gray, or different "brightness" in a two-dimensional image. Such images, also referred to as B-mode images, may display a two-dimensional cross-section of the tissue being imaged. In some exemplary embodiments, other ultrasound imaging modalities may be used, such as for example, A-mode, C-mode, M-mode, Doppler-mode, or the like. In some exemplary embodiments, the ultrasonic image may be a 2D image of a plane of the tissue, a 3D image of the tissue, or the like.

One technical solution is to identify an artifact within the image and search for the tissue segment in a location adjacent to the artifact. The artifact may be a misrepresentation of the tissue structure associated with the imaging modality of the image. In some exemplary embodiments, the artifact may refer to something seen on the image that may not exist in reality. The artifact may be helpful interpreting the image, but may potentially confuse the person who examines of the image as it is a distortion of the tissue being imaged.

It will be noted that the disclosed subject matter is not limited to any specific form of artifact or any imaging modality. However, for the purpose of clarity and without limiting the disclosed subject matter, the disclosed subject matter is exemplified with respect to ultrasonic images. One example of an artifact in ultrasound images may be caused by an attenuation. Attenuation in ultrasound may be the reduction in amplitude of an ultrasound beam as a function of distance through an imaging medium.

In some exemplary embodiments, the artifact may be a posterior amplification artifact, a posterior attenuation artifact, or the like. A posterior attenuation artifact may be caused by partial or total reflection or absorption of a sound energy. A weaker signal may return from behind a strong reflector, or a sound absorbing structure, such as a gallstone, a bone or the like. In the case of a posterior amplification artifact, the area behind an echo-weak or echo-free structure may appear brighter (more echogenic) than its surrounding structures. This may occur because neighboring signals may have passed through more attenuating structures and return with weaker echoes.

For example, in some exemplary embodiments, when the tissue segment is a tumor, in some cases, the tumor may have a high attenuation in comparison to the surrounding tissue. In such cases, the area below the tumor may appear darker due to the attenuation (e.g., a posterior attenuation artifact). In other cases, the tumor may have a low attenuation in comparison to the surrounding tissue. In such cases, the area below the tumor may be brighter (e.g., a posterior amplification artifact).

In some exemplary embodiments, searching for the tissue segment may be in a location that is shallow to the artifact with respect to the source emitting the ultrasound waves (e.g., that is anterior to the artifact). Additionally or alternatively, searching for the tissue segment may be limited by about the side borders of the artifact, which may be identified during the identification of the artifact.

In some exemplary embodiments, identifying the artifact may comprise identifying an upper border of the artifact, and the searching may comprise detecting a gray level directly over a center of the upper border of the artifact and applying a region growing algorithm based on the gray level detected over the center of the upper border, to automatically identify the tissue segment.

One technical effect of utilizing the disclosed subject matter is to automatically identify target tissue segment even in cases where the segment itself does not appear clearly in the image. In some cases, more reliable automatic segmentation identification may be achieved by relying on artifacts that are visible in the image and may provide information that is useful to the segmentation process. In some exemplary embodiments, the disclosed subject matter may be useful to provide for a decision support system that may assist professionals in identifying tissue segments in the image, such as tumors. The decision support system may also overcome the disadvantages of manual operation, such as human error, time consumption, and the like.

Figure 1:
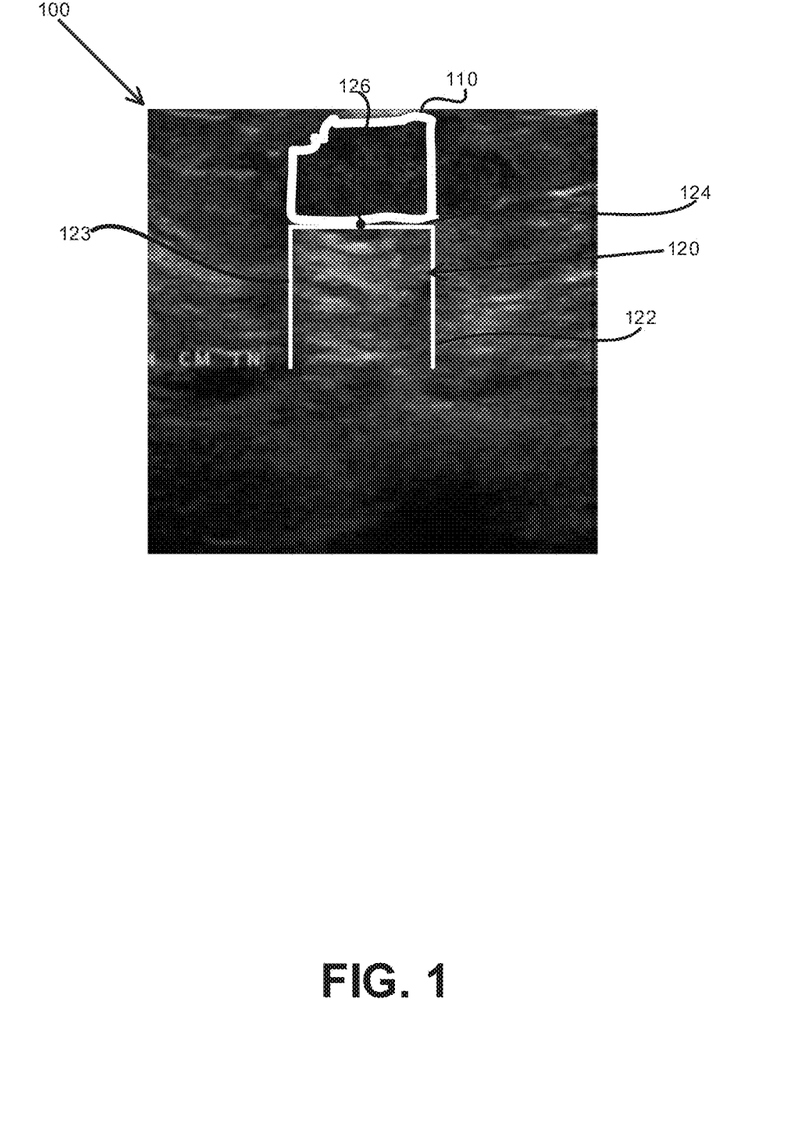
FIG. 1 shows an illustration of an image, in accordance with some exemplary embodiments of the subject matter.

Referring now to FIG. 1 showing an illustration of an image, in accordance with some exemplary embodiments of the subject matter.

In some exemplary embodiments, an Image 100 may be a medical imaging, such as for example a B-mode ultrasonic image. It will be noted that the disclosed subject matter is not limited to ultrasonic images, any image may be obtained, such as MRI image, 3D ultrasonic image or the like. Image 100 may be an image of an anatomical tissue. As an example only, the anatomical tissue may be a breast of a woman, and a Tissue Segment 110 to be identified by the disclosed subject matter may be a breast tumor.

In some exemplary embodiments, an Artifact 120 may be identified within Image 100. Artifact 120 may be a posterior amplification artifact, which may appear brighter (more echogenic) than its surrounding structures at a same depth. In some exemplary embodiments, Artifact 120 may be caused by partial or total reflection or absorption of a sound energy. In some exemplary embodiments, the area of Artifact 120 may be behind an echo-weak or echo-free structure, such as Tissue Segment 110. In other examples, Artifact 120 may be another kind of artifact, such as a posterior attenuation artifact or the like. In some exemplary embodiments, a Left Side Border 123 and a Right Side Border 122 of Artifact 120 may be identified. Searching for Tissue Segment 110 may be limited by about Side Borders 122, 123 of Artifact 120.

In some exemplary embodiments, an Upper Border 124 of Artifact 120 may be identified. In some exemplary embodiments, a Center 126 of Upper Border 124 may be identified. The automatic search for Tissue Segment 110 may commence at Center 126. In some exemplary embodiments, a growing algorithm may be used and initialized with Center 126 (or a point directly above it). The region growing algorithm may be based on the gray level detected over Center 126 and may be utilized to automatically identify Tissue Segment 110. In some exemplary embodiments, the region growing may be bounded by about Side Border 122, 123.

Figure 2:
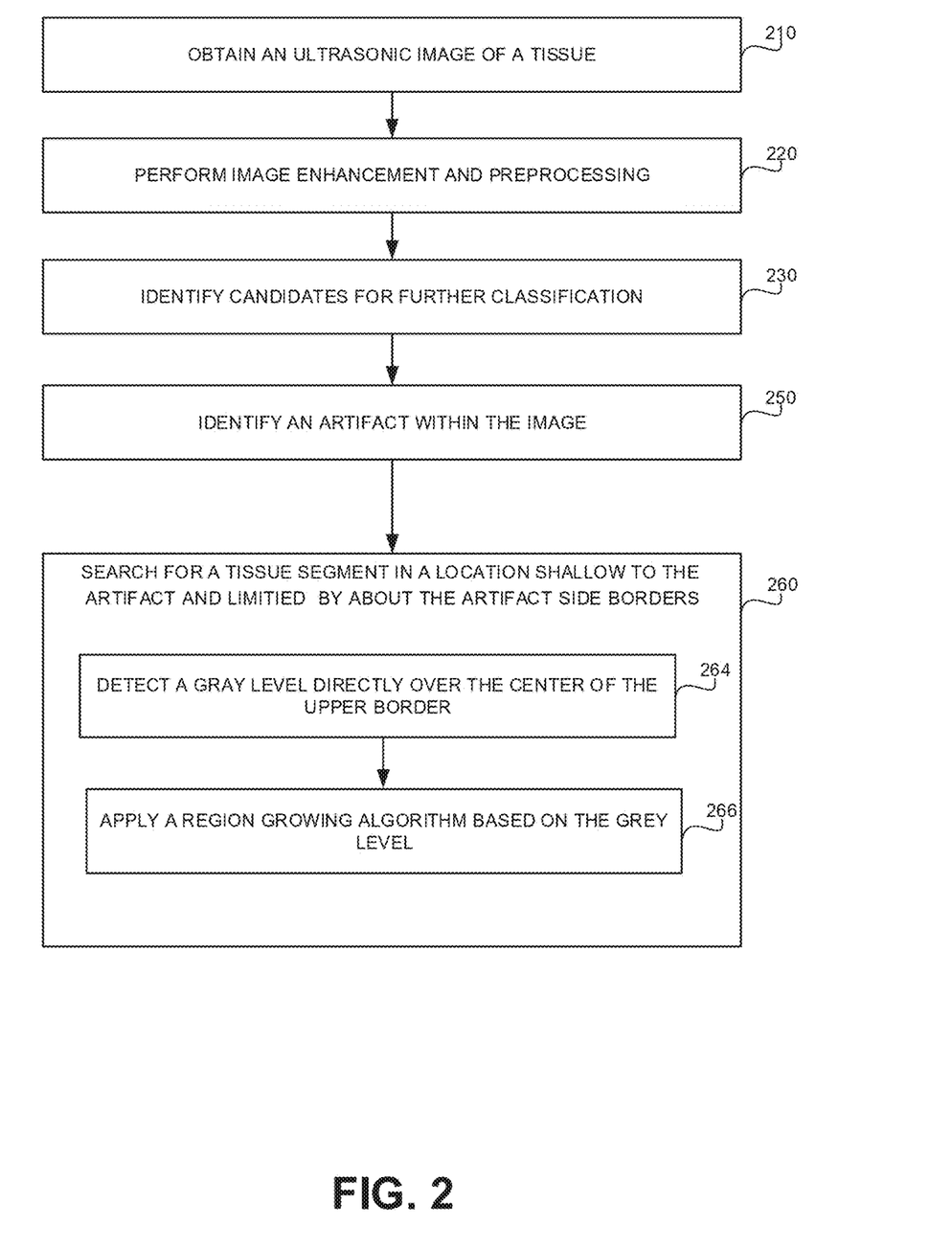
FIG. 2 shows a flowchart diagram of a method, in accordance with some exemplary embodiments of the disclosed subject matter.

Referring now to FIG. 2 showing a flowchart diagram of a method, in accordance with some exemplary embodiments of the disclosed subject matter.

In Step 210, an ultrasonic image of a tissue may be obtained. The ultrasonic image may be a B-mode image which may display a two-dimensional cross-section of an anatomical tissue being imaged. The image may be obtained from a medical imaging device, may be retrieved from a repository, or the like.

As an example only, the anatomical tissue may be a breast of a woman, and the tissue segment to be identified by the method may be a breast tumor, that may be later analyzed to be either malignant or benign.

In Step 220, image enhancement and preprocessing may be performed over the ultrasonic image.

In some exemplary embodiments, Time-Gain compensation may be performed to enhance the image. Time-Gain Compensation may utilize a Time-Gain compensation curve which may account for tissue attenuation. By increasing the received signal intensity with depth, imaging modality (such as B-mode) may provide for a relatively uniform representation of similar tissue at different depths.

Additionally or alternatively, speckle removal may be performed to enhance the image. Additional or alternatively, resolution enhancement, contrast enhancement (e.g., using frequency-domain techniques) to suppress speckle; imaging of spectral parameters (which may sense the sizes and concentrations of sub-resolution tissue constituents), combinations of spectral parameters and ancillary clinical data (e.g., PSA blood levels) or the like may be performed in order to enhance the image and as part of the image preprocessing.

In Step 230, artifact candidates may be identified within the ultrasonic image. The candidates may be automatically identified as potential artifacts in the image.

In some exemplary embodiments, Maximally Stable Extremal Regions (MSER) procedure may be performed to yield blobs of pixels that may represent the candidates for further classification. MSER procedure may determine regions based solely on an extremal property of an intensity function in a region and its outer boundary. Additionally or alternatively, MSER may determine the regions based on additional features. Other techniques, such as for example watershed, may also be used to identify the candidates.

In Step 250, an artifact may be identified within the image. The artifact may be a misrepresentation of the anatomical tissue structure. In some exemplary embodiments, a candidate identified in Step 230 may be classified as an artifact.

In some exemplary embodiments, a median gray level of the tissue may be estimated, and patches of posterior attenuation or posterior amplification may be identified as artifacts. Posterior attenuation or posterior amplification may indirectly indicate tissue segment presence.

In some exemplary embodiments, identifying the artifact within the image may comprise identifying side borders of the artifact. Additionally or alternatively, identifying the artifact within the image may comprise identifying an upper border of the artifact.

In Step 260, a tissue segment may be searched for based on the location of the artifact. In some exemplary embodiments, the tissue segment may be searched for, in a location shallow to the artifact. In some exemplary embodiments, the tissue segment may be searched for in a location shallow to a posterior artifact. Searching for the tissue segment may be limited by about the artifact side borders, such as that the tissue segment may be searched for in a location anterior to the artifact and which is limited by the side borders of the artifact. In some exemplary embodiments, the side borders may provide a limitation on the width of the segment. As an example, the limitation may be exactly the side borders, ten pixels wider than the width defined by side borders, five pixels narrower than the width defined by the side borders, or the like. In some exemplary embodiments, the limitation may be any number of pixels between 0 and 20, wider or narrower than the width defined by side borders. Additionally or alternatively, the limitation may be 10% more or less than the precise width defined by the side borders of the artifact.

In Step 264, a gray level may be detected directly over the center of the upper border of the artifact. In some exemplary embodiments, the ultrasound imaging modality may display small differences in acoustical impedance as different gray levels. The ultrasound imaging modality may produce basically black and white images with series of levels of gray. Solid areas may appear white and fluid areas may appear black, varying from black at the weakest intensity to white at the strongest. A pixel or pixels appearing at about the center of the upper border of the artifact, e.g., anterior to the upper border of the artifact, may be identified. It will be noted that the gray level may be sampled from one or more pixels, appearing precisely at the center of the upper border of the artifact, or in a location close by, such as offset by 10% to one side, offset by twenty pixels to one side, or the like.

In Step 266, a region growing algorithm may be applied, based on the gray level detected in Step 264.

In some exemplary embodiments, region growing may be initialized with an initial region based on the pixels identified in Step 264. The region growing may iteratively increase the initial region to detect the tissue segment. In some exemplary embodiments, a region may be grown from the seed point to adjacent points depending on a region membership criterion, which may be the gray level. The region growing algorithm may keep examining adjacent pixels of the seed point. If the adjacent pixels have the same intensity value with the seed point, the region growing algorithm may classify them into seed points. It may be an iterated process until there may be no change in two successive iterative stages and the region cannot be grown more. In some exemplary embodiments, the region growing may be limited by about the side borders of the artifact and would therefore not grow a region exceeding the side borders even if the gray levels are considered suitable for being included in the region.

Figure 3:
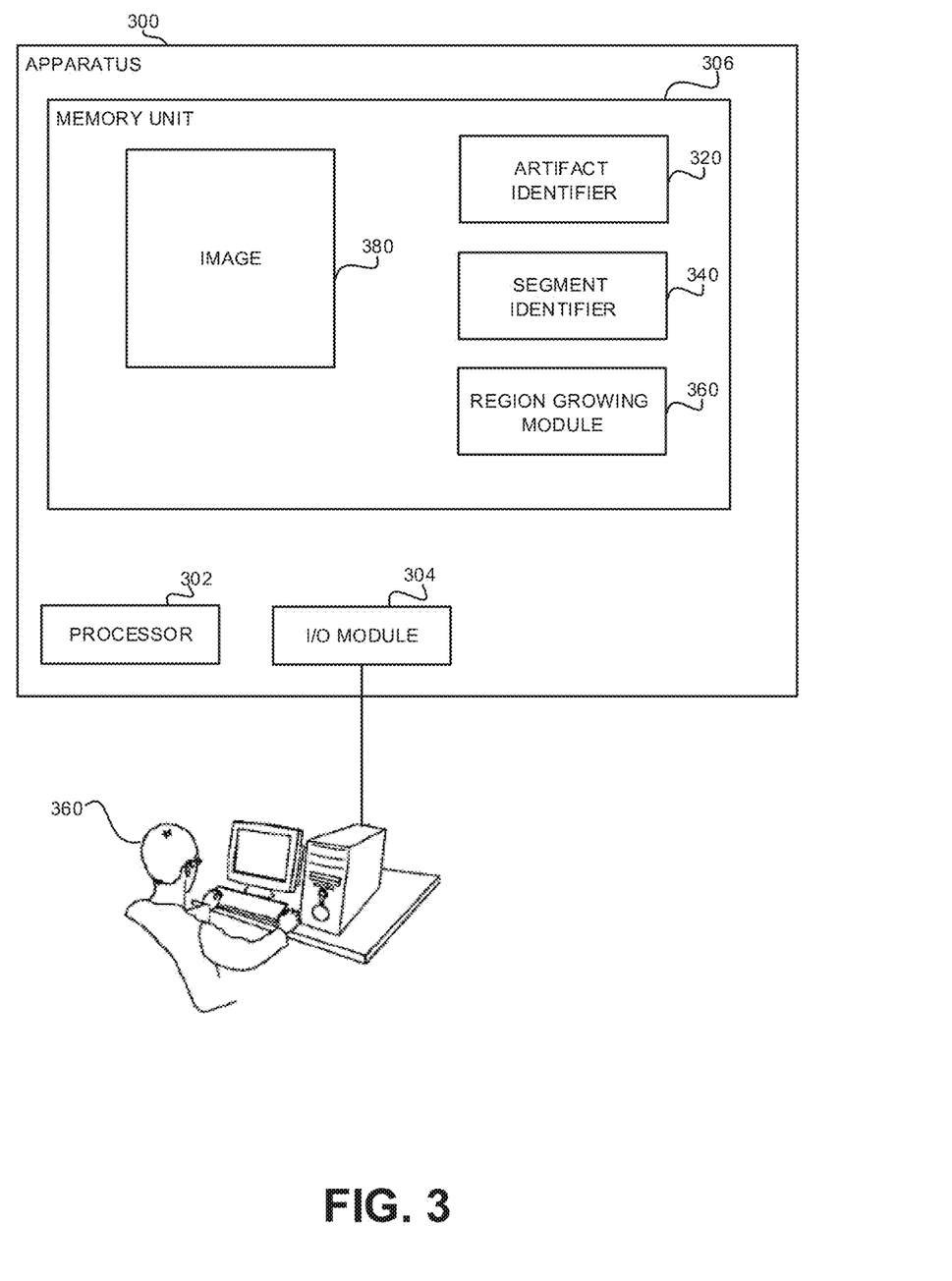
FIG. 3 shows a block diagram of an apparatus, in accordance with some exemplary embodiments of the disclosed subject matter.

Referring now to FIG. 3 showing an apparatus, in accordance with some exemplary embodiments of the disclosed subject matter. An Apparatus 300 may be configured to identify a tissue segment within an Image 380, in accordance with the disclosed subject matter. Additionally or alternatively, Apparatus 300 may be configured to perform the method depicted in FIG. 2.

In some exemplary embodiments, Apparatus 300 may comprise a Processor 302. Processor 302 may be a Central Processing Unit (CPU), a microprocessor, an electronic circuit, an Integrated Circuit (IC) or the like. Processor 302 may be utilized to perform computations required by Apparatus 300 or any of it subcomponents.

In some exemplary embodiments of the disclosed subject matter, Apparatus 300 may comprise an Input/Output (I/O) Module 304. I/O Module 304 may be utilized to provide an output to and receive input from a User 360. It will be noted that User 360 may or may not be an expert in the field of segmentation of Image 380, such as a radiologist, a physician, or the like. In some exemplary embodiments, Apparatus 300 may operate without having a user. I/O Module 304 may be used to obtain Image 380. I/O Module 304 may be used to output the location of a tissue segment, such as 110 of FIG. 1, within Image 380.

In some exemplary embodiments, Apparatus 300 may comprise a Memory Unit 306. Memory Unit 306 may be a hard disk drive, a Flash disk, a Random Access Memory (RAM), a memory chip, or the like. In some exemplary embodiments, Memory Unit 306 may retain program code operative to cause Processor 302 to perform acts associated with any of the subcomponents of Apparatus 300.

In some exemplary embodiments, Image 380 may be a clinical image of an anatomical tissue. Image 380 may be produced using an imaging modality. In some exemplary embodiments, Image 380 may be an ultrasonic image. Additionally or alternatively, Image 380 may be a B-mode ultrasonic image, such as 100 of FIG. 1, produced by a brightness-mode (B-mode) ultrasound imaging modality.

In some exemplary embodiments of the disclosed subject matter, Apparatus 300 may comprise, a Segment Identifier 340. Segment Identifier 340 may be utilized to identify a segment within Image 380. In some exemplary embodiments, when Image 380 is a medical image of an anatomical tissue, Segment Identifier 340 may identify a tissue segment within Image 380. Segment Identifier 340 may search for the segment based on an artifact within Image 380, such as an artifact identified by an Artifact Identifier 320. In some exemplary embodiments, Segment Identifier 340 may utilize a Region Growing Module 360 to identify the segment and may utilize borders of the artifact to perform its search, such as by searching in a location shallow to the artifact, by initializing the search above the center of the upper border of the artifact, by limiting the search to the side borders of the artifact, or the like.

In some exemplary embodiments of the disclosed subject matter, Apparatus 300 may comprise Artifact Identifier 320. Artifact Identifier 320 may be utilized to identify an artifact within Image 380, such as 110 in FIG. 1.

In some exemplary embodiments of the disclosed subject matter, Apparatus 300 may comprise Region Growing Module 360. Region Growing Module 360 may be utilized to perform a region growing algorithm, to identify a location of tissue segment, such as described in Step 266 in FIG. 2. In some exemplary embodiments, Region Growing Module 360 may enforce a limitation on the region growing that is based on the side borders of the artifact. In some exemplary embodiments, the region may not be grown in a way exceeding the side borders, even if the same gray level exits beyond the side borders of the artifact.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
   obtaining an image of a tissue, wherein the image is produced using an imaging modality;
   automatically identifying, by a processor, a tissue segment within the image, wherein said identifying comprises:
      identifying an artifact within the image, wherein the artifact is a misrepresentation of a tissue structure appearing brighter or darker than one or more surrounding structures at a same depth, wherein the misrepresentation is associated with the imaging modality, wherein said identifying the artifact comprises:
         employing an image processing procedure for determining regions of local extremal intensity; and
         determining regions having a different intensity level than surrounding regions thereof;
      and
      searching for the tissue segment in a location adjacent to the artifact, wherein said searching comprises:
         detecting a point at about a center of an upper border of the artifact; and
         applying a region growing algorithm to automatically identify the tissue segment, wherein the region growing algorithm is initialized to include the point
      wherein said identifying the artifact comprises identifying side borders of the artifact, wherein said searching is limited by about the side borders.

2. The computer-implemented method of claim 1, wherein the image is an ultrasonic image.

3. The computer-implemented method of claim 2, wherein the imaging modality is a brightness-mode ultrasound imaging modality.

4. The computer-implemented method of claim 3, wherein the artifact is selected from the group of: posterior amplification and posterior attenuation.

5. The computer implemented method of claim 3, wherein the ultrasonic image is created using ultrasound waves emitted from a source, wherein said searching comprises searching for the tissue segment in a location that is shallow to the artifact with respect to the source.

6. The computer-implemented method of claim 1, wherein the tissue segment is a tumor.

7. A computerized apparatus having a processor, the processor being adapted to perform the steps of:
   obtaining an image of a tissue, wherein the image is produced using an imaging modality;
   automatically identifying a tissue segment within the image, wherein said identifying comprises:
      identifying an artifact within the image, wherein the artifact is a misrepresentation of a tissue structure appearing brighter or darker than one or more surrounding structures at a same depth, wherein the misrepresentation is associated with the imaging modality, wherein said identifying the artifact comprises:
         employing an image processing procedure for determining regions of local external intensity; and
         determining regions having a different intensity level than surrounding regions thereof; and
      searching for the tissue segment in a location adjacent to the artifact, wherein said searching comprises:
         detecting a point at about a center of an upper border of the artifact; and
         applying a region growing algorithm to automatically identify the tissue segment, wherein the region growing algorithm is initialized to include the point
      wherein said identifying the artifact comprises identifying side borders of the artifact, wherein said searching is limited by about the side borders.

8. The computerized apparatus of claim 7, wherein the image is an ultrasonic image.

9. The computerized apparatus of claim 8, wherein the artifact is selected from the group of: posterior amplification and posterior attenuation.

10. The computerized apparatus of claim 8, wherein the ultrasonic image is created using ultrasound waves emitted from a source, wherein said searching comprises searching for the tissue segment in a location that is shallow to the artifact with respect to the source.

11. The computerized apparatus of claim 7, wherein the tissue segment is a tumor.

12. A computer program product comprising a computer readable storage medium retaining program instructions, which program instructions when read by a processor, cause the processor to perform a method comprising:
   obtaining an image of a tissue, wherein the image is produced using an imaging modality;
   automatically identifying a tissue segment within the image, wherein said identifying comprises:

identifying an artifact within the image, wherein the artifact is a misrepresentation of a tissue structure appearing brighter or darker than one or more surrounding structures at a same depth, wherein the misrepresentation is associated with the imaging modality, wherein said identifying the artifact comprises:
   employing an image processing procedure for determining regions of local external intensity; and
   determining regions having a different intensity level than surrounding regions thereof; and
searching for the tissue segment in a location adjacent to the artifact, wherein said searching comprises:
   detecting a point at about a center of an upper border of the artifact; and
   applying a region growing algorithm to automatically identify the tissue segment, wherein the region growing algorithm is initialized to include the point
wherein said identifying the artifact comprises identifying side borders of the artifact, wherein said searching is limited by about the side borders.

* * * * *